US00PP32029P2

(12) United States Plant Patent
Slaughter et al.

(10) Patent No.: US PP32,029 P2
(45) Date of Patent: Aug. 4, 2020

(54) ***PRUNUS* ROOTSTOCK, 'WAROOTONE'**

(50) Latin Name: [*Prunus dulcis* x *Prunus persica*] x [*Prunus davidiana* x *Prunus persica*]
Varietal Denomination: Warootone

(71) Applicant: Wawona Packing Co., LLC, Cutler, CA (US)

(72) Inventors: John Keith Slaughter, Fresno, CA (US); Kaylan M. Roberts, Fresno, CA (US)

(73) Assignee: Wawona Packing Company, LLC, Cutler, CA (US)

( * ) Notice: Subject to any disclaimer, the term of this patent is extended or adjusted under 35 U.S.C. 154(b) by 0 days.

(21) Appl. No.: 16/602,417

(22) Filed: Sep. 30, 2019

(51) Int. Cl.
*A01H 5/00* (2018.01)
*A01H 6/74* (2018.01)

(52) U.S. Cl.
USPC ..... Plt./180

(58) Field of Classification Search
USPC ..... Plt./180
CPC ..... A01H 5/00; A01H 6/74
See application file for complete search history.

(56) References Cited

U.S. PATENT DOCUMENTS

PP21,248 P2 8/2010 Slaughter et al.

*Primary Examiner* — Annette H Para
(74) *Attorney, Agent, or Firm* — Potter Anderson and Corroon LLP

(57) ABSTRACT

A new and distinct variety of *Prunus* rootstock tree ([*Prunus dulcis* x *Prunus persica*] x [*Prunus davidiana* x *Prunus persica*]), which is denominated varietally as 'Warootone', which when utilized as a rootstock reduces the growth and height of fruiting cultivars of peach, nectarine, plum, almond, and apricot.

3 Drawing Sheets

Botanical designation: [*Prunus dulcis* x *Prunus persica*] x [*Prunus davidiana* x *Prunus persica*].
Varietal denomination: 'Warootone'.

BACKGROUND OF THE NEW VARIETY

The present invention relates to a new, novel, and distinct variety of a *Prunus* hybrid rootstock tree, [*Prunus dulcis* x *Prunus persica*] x [*Prunus davidiana* x *Prunus persica*], and which has been denominated varietally as 'Warootone'.

The present variety of rootstock tree resulted from an on-going program of fruit tree and rootstock breeding. The purpose of this program is to improve the commercial quality of deciduous fruit varieties, and rootstocks, by creating and releasing promising selections of *Prunus* species and interspecific hybrids thereof. To this end we make both controlled and hybrid cross pollinations each year to produce seedling populations from which improved progenies are evaluated and selected.

The seedling, 'Warootone' was originated by the breeders at Wawona Packing Company and selected from a population of seedlings growing in our experimental orchards which are located near Fowler, Calif., USA. The seedlings, grown on their own roots, were derived from planting seed of a Wawona Packing Company Rootstock 'Cornerstone' (U.S. Plant Pat. No. 21,248), [*Prunus dulcis*, 'Titan' {92-54 USDA/Cal State Fresno release, unpatented} X *Prunus persica*, 'Nemared' {unpatented}], used as the female parent. The pollen parent used to create this seedling was a seedling of *Prunus davidiana* x *Prunus persica*, non-patented. The resulting fruit of this cross was collected from the female parent at a mature stage and seeds were extracted in September of 2000. After a period of stratification, the seed was placed in the greenhouse by population, and then field planted for tree establishment and observation. One seedling, which is the present variety, exhibited especially desirable characteristics, and was then designated as 'D63.182'. This seedling was marked for subsequent observation. After the 2005 growing season, the new variety of rootstock tree was selected for clonal repropagation, scion compatibility, rooting percentage studies, nematode screening, and advanced evaluation.

ASEXUAL REPRODUCTION

Asexual reproduction of this new and distinct variety of rootstock tree was accomplished by preparing approximately 50 dormant cuttings, applying an auxin (indolebutryic acid) to the basal end of the cutting, and planting the new rootstock tree directly onto virgin soil. This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Warootone' is a new and distinct variety of rootstock tree, which is considered of moderate in size, and which has a moderate growth characteristic. This new rootstock tree is also exhibiting the ability to initiate roots from vegetative cuttings and then produce trees from said cuttings with a very high rate of success.

This new rootstock has a medium high chilling requirement of approximately 750 hours. The 'Warootone' rootstock tree, when grafted to compatible species, produces a tree canopy at maturity that is approximately 20% smaller than trees of the same scion variety grafted to the common commercially used 'Nemaguard' rootstock (un-patented USDA Release). Trunk cross sectional comparisons between 'Warootone' and 'Nemaguard' have consistently shown approximately a 20% reduction in the dimensions of 'Warootone' when compared to 'Nemaguard' rootstock with trees of the same age and cultural management. Reduced tree height and trunk cross sectional were also recorded in 'Warootone' when compared to its female parent 'Cornerstone' and its male parent (unpatented) by approximately 45%. 'Wawrootone' has exhibited resistance to the major species of root-knot nematodes (*Meloidogyne* nematodes) prevalent in the Southern San Joaquin Valley of Central Calif. Additionally, 'Warootone' has shown resistance to ring nematode (*Criconemoides xenoplax*) also common in the soils of this commercial fruit and almond growing region. During 10 years of internal trials, 'Warootone' has displayed full graft compatibility with commercial peach, nectarine, plum, and almond species. To date, 'Warootone' has exhibited graft compatibility with the apricots that has been tested with.

Figure 1:
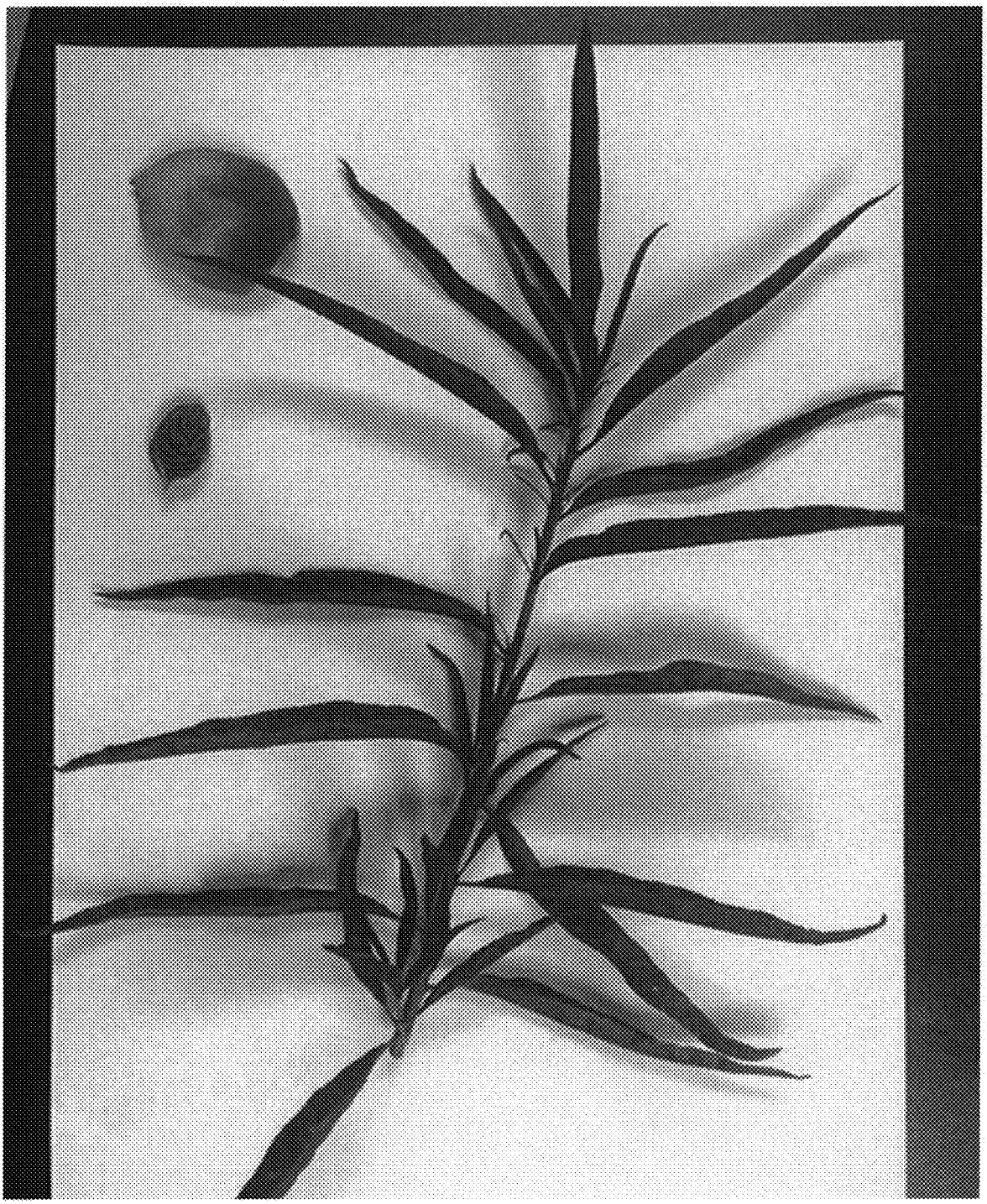
FIG. 1 is a color photograph of characteristic leaves of current seasons growth, a typical fruit, and typical stone from the current variety.
Figure 2:
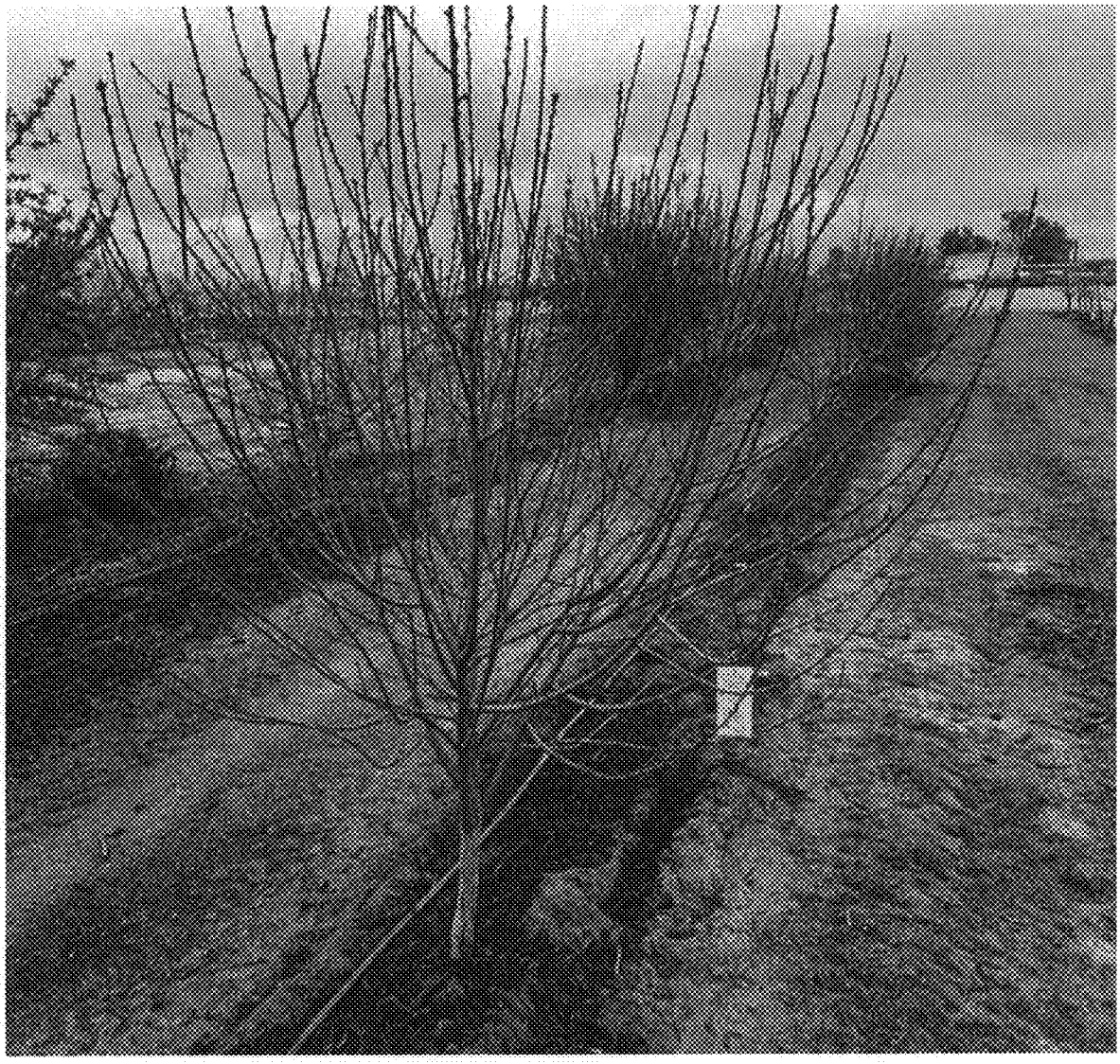
FIG. 2 is a color photograph of a dormant, ungrafted 2-year-old tree of the current variety displaying the general growth pattern, primary limb angles, and branching characteristics.
Figure 3:
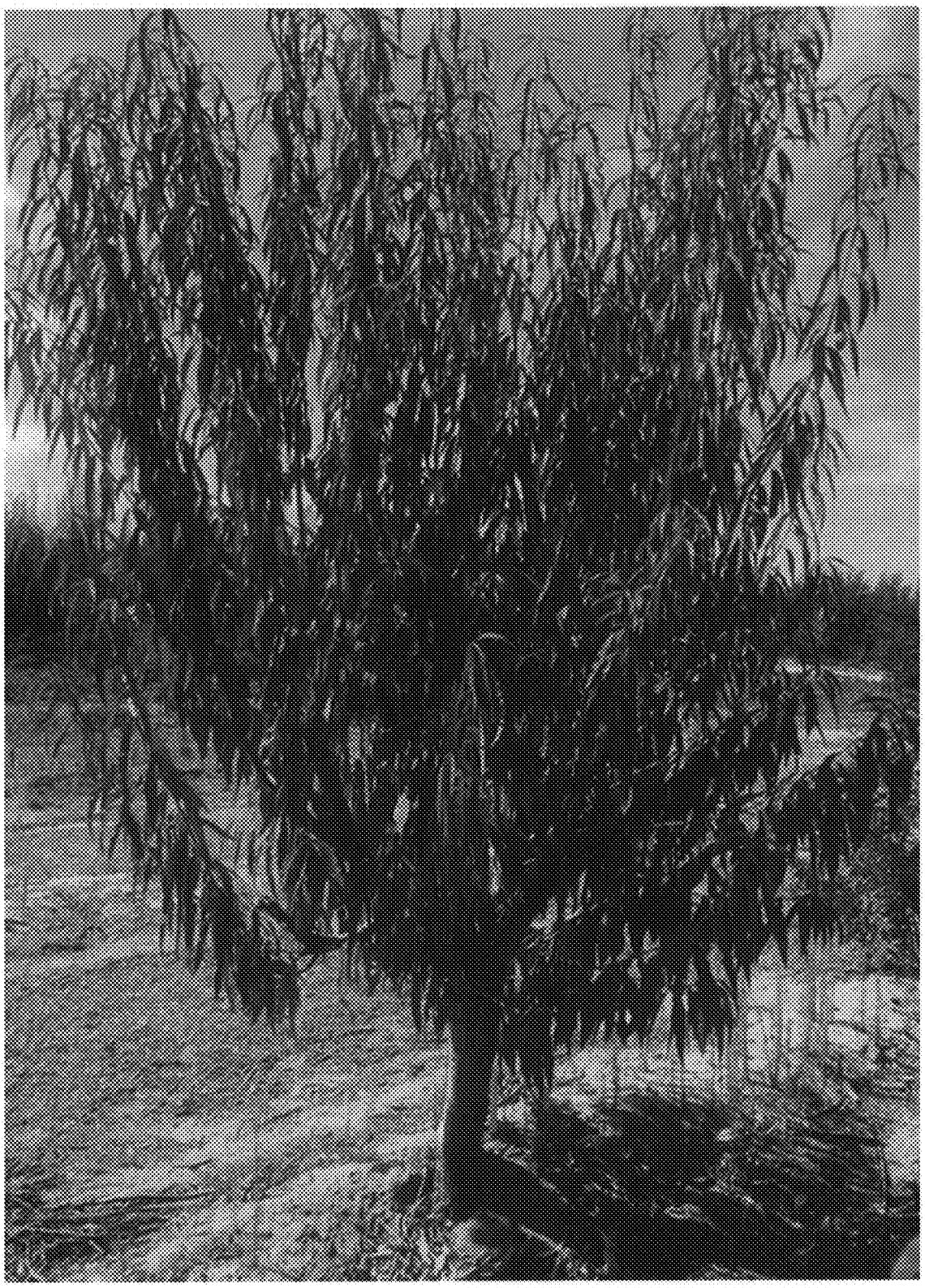
FIG. 3 is a color photograph of an ungrafted, 3-year-old tree in foliage.

Due to chemical development, processing and printing, the leaves and fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. § 112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any purpose, or non-infringement which is directed, in whole, or in part, to the present variety.

DETAILED DESCRIPTION

Referring more specifically to the pomological details of this new and distinct variety of rootstock, the following has been observed during the tenth fruiting season, and under the ecological conditions prevailing at the orchards of the assignee which are located near the town of Fowler, county of Fresno, state of California. All major color code designations are by reference to The R.H.S. Colour Chart (Royal Horticultural Society, Fourth Edition, 2001) provided by The Royal Horticultural Society of Great Britain. Common color names are also occasionally used.

TREE

Size: Generally considered medium to medium small in its growth habit as compared to other common commercial rootstocks currently used in orchard practices. The tree of the present variety was pruned to a height of about 250.0 cm. to about 300.0 cm. at maturity.

Width: Approximately 175.0 cm.

Vigor: Considered medium vigor. The present rootstock tree variety grew from about 120.0 cm. to about 140.0 cm. in height during the first growing season.

Productivity: Poor. Fruit production is very low.

Fruit bearing: Regular. Fruit set and production has been sparse historically. The current variety is intended to be reproduced from vegetative cuttings and or tissue culture multiplication and not from the production of a seed crop.

Tree form: Very upright.

Density: Considered open without excessive subterminal branching.

Hardiness: The present tree was grown and evaluated in USDA Hardiness Zone 9. The calculated winter chilling requirements of the new tree is approximately 750 hours at a temperature below 7.0 degrees C. The present variety appears to be hardy under typical central San Joaquin Valley climatic conditions.

TRUNK

Diameter: Approximately 22.0 cm in diameter when measured at approximately 15.5 cm. above the soil level. This measurement was taken at the beginning of the 8th growing season.

Bark texture: Considered moderately rough, with folds of papery scarfskin being present. Since bark development and coloration change with advancing tree age this characteristic varies with the tree vigor, age, and regional conditions. Therefore, this is not a dependable descriptor of the new variety.

Lenticels: Numerous flat, oval lenticels are present. The lenticels range in size from about 4.0 millimeters to about 6.0 mm. in width, and between about 1.0 and about 2.5 millimeters in height. The development and size of the trunk lenticels can be influenced, to some degree, by the ambient growing conditions, and are not, necessarily, a dependable characteristic of this variety. As trees of this variety mature, lenticels are present, but they are generally covered by increasing layers of cork (mature bark) and therefore become less apparent.

Lenticel color: Considered an orange brown, (RHS Greyed-Orange Group 165 B).

Bark coloration: Variable, but it is generally considered to be a greyed tan, (RHS Greyed-White Group 157 B). This bark description was taken from trees in their tenth leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

BRANCHES

Size: Considered medium small for the species.

Diameter: Medium small as compared to other commercial hybrid rootstock varieties. The branches have a diameter of about 11.0 centimeters when measured during the 8th growing season.

Flowering shoot thickness: Average for the species. Generally, the most consistent flower bud development and therefore potential fruiting sites occur on shoots which are about 9.0 millimeters in diameter or larger but generally less than about 12.0 millimeters in diameter at the time of bloom.

Surface texture: Average and appearing relatively smooth.

Crotch angles: Primary branches are considered relatively acute and upright and are usually growing at an angle of about 55 to about 60 degrees when measured from a horizontal plane.

Current season shoots: Surface texture—Substantially glabrous.

Internode length: Approximately 2.0 cm.

Color of mature branches: Approximately Grey brown, (RHS Greyed-Green Group 197 C).

Current season's shoots: Color.—Light green, (RHS Yellow-Green Group 145 C). The color of new shoot tips is considered a deep shiny red (RHS Greyed-Purple Group 187 C). The most recently formed shoot tips exhibit this red color. The lower vegetative shoot color transitions with advancing maturity to light green.

LEAVES

Size: Considered somewhat elongated and narrow for the species. Leaf measurements have been taken from vigorous, upright, current-season growth, at approximately mid-shoot. The leaf size is often influenced by prevailing growing conditions, quality and intensity of available sunlight, and the location of the leaf within the tree canopy. For this reason, leaves sizes can vary significantly based upon the ambient light and other cultural factors listed above and are not typically considered a dependable botanical descriptor.

Leaf length: About 142.0 to about 175.0 millimeters (including the petiole).

Leaf width: About 27.0 to about 35.0 millimeters.

Leaf base-shape: The leaves generally exhibit unequal marginal symmetry relative to the leaf longitudinal axis.

Leaf form: Lanceolate.

Leaf tip form: Acuminate.

Leaf color: Upper Leaf Surface—Medium green, (approximately RHS Green Group 137 B).

Leaf texture:

*Upper leaf surface*.—Glabrous.

*Lower leaf surface*.—Glabrous.

Leaf color: Lower Leaf Surface—Medium green, (approximately RHS Green Group 137 C).

Leaf venation: Pinnately veined.

Mid-vein: Color—Considered a pale pink, (approximately RHS Yellow-Green Group 35 C).

Leaf margins: Gently undulating.

*Form*.—Considered crenulate.

*Uniformity*.—Generally uniform.

Leaf petioles:

*Form*.—Considered canaliculated and having a more pronounced trough when viewed from the dorsal aspect. The petiole margin is considered rounded when viewed from the ventral aspect.

*Size*.—Considered medium for the species.

*Length*.—About 9.0 to about 12.0 mm.

*Diameter*.—About 1.5 to about 2.0 mm.

*Color*.—A yellowed green, (approximately RHS Yellow-Green Group 146 D).

*Texture*.—Glabrous.

*Strength*.—Durable for species until senescence.

Leaf glands:

*Size*.—Considered relatively small for the species; about 2.0 mm. in width; and about 2.0 mm. in height.

*Number*.—Generally, one and less common two glands appear per marginal side are found. Observations of more than two glands per marginal side are very uncommon.

*Type*.—Glands located at the base of the leaf are predominantly globose in shape. An additional one to two, or occasionally more glands, which appear reniform, and stalked, gland primordia are often present at the basal margin of the leaf as well.

*Color*.—Considered a yellowed greed, approximately (RHS Yellow-Green Group 151 B). Typically, the coloration of the glands darkens, and occasionally begins to desiccate relatively early in the growing season.

Leaf stipules:

*Size*.—Very large for this variety. About 9.0 to about 15.0 millimeters in length. About 1.0 to about 2.0 millimeters in width.

*Number*.—Typically, 2 per leaf bud, and up to 6 per shoot tip.

*Form*.—Lanceolate in form and having an extremely serrated marginal edge.

*Color*.—Red Green, (approximately RHS Greyed-Red Group 181 B) when young, but graduating to a brown color, (approximately RHS Greyed-Orange Group 165 A) with advancing senescence. The leaf stipules are generally considered to be early deciduous.

FLOWER BUDS

Hardiness: No winter injury (bud death) has been noted during the last several years of observation in the central San Joaquin Valley. The new variety of *Prunus* rootstock tree has not been intentionally subjected to drought, cold or heat stress, and therefore this information is not available.

Flower bud: Size—Generally small and variable for the genus. The flower buds as described were observed approximately 7 days prior to bloom.

Length: Approximately, 12.5 millimeters.

Diameter: Approximately, 9.5 millimeters.

Surface texture: Pubescent.

Orientation: Considered appressed but appear less so as the blossoms near opening.

Bud scale color: Approximately RHS Greyed-Orange Group 175 A.

FLOWERS

Date of first bloom: Observed on Mar. 14, 2019.

Blooming time: Considered average to slightly mid-late in relative comparison to other commercial rootstock cultivars grown in the Central San Joaquin Valley. The date of full bloom was observed on Mar. 19, 2019. The date of full bloom varies slightly with climatic conditions, and prevailing cultural practices.

Duration of bloom: Approximately 12 or more days. This characteristic varies slightly with the prevailing climatic conditions.

Flower class: Considered a perfect flower, complete and perigynous.

Flower type: The variety is considered to have a non-showy type flower.

Flower size: Considered small. The flower diameter at full bloom, is about 14.0 to about 19.0 millimeters.

Bloom quantity: Considered low.

Flower bud density: Generally considered sparse.

Flower bud frequency: Generally infrequent, 1 flower bud or less appear per node.

Petal size: Generally considered small for the species.

*Petal length.*—About 8.0 to about 11.0 millimeters.

*Petal width.*—About 7.0 to about 9.0 millimeters.

Petal form: Considered broadly ovate.

Petal count: Nearly always 5.

Petal texture:

*Upper petal texture.*—Very finely pubescent, satin like.

*Lower petal texture.*—Very finely pubescent, satin like.

Petal color: Considered a light pink at the popcorn stage, (RHS Greyed-Red Group 179 D).

Fragrance: Slight.

Petal claw:

*Form.*—The claw is considered ovate and is generally large.

*Length.*—Approximately 5.0 millimeters.

*Width.*—Approximately 4.0 millimeters.

Petal margins: Generally, slightly undulate.

Petal apex: Entire.

Flower pedicel:

*Length.*—Considered medium with a length of about 2.5 to about 3.5 millimeters.

*Diameter.*—About 1.5 to about 2.0 millimeters.

*Color.*—A pale green with bud scales removed, approximately (RHS Yellow-Green Group 150 B) depending on pedicel and fruit maturity and timing of visual observance.

*Strength.*—Tenacious. Average for the species.

*Texture.*—Generally smooth to slightly undulate.

Floral nectaries:

*Color.*—Considered a pale green, (approximately RHS Yellow-Green Group 145 B).

Calyx:

*Surface texture.*—Generally glabrous.

*Color.*—Approximately RHS Greyed-Red Group 178 C.

Sepals:

*Upper surface texture.*—Moderately pubescent.

*Lower surface texture.*—Slight pubescence.

*Number.*—5 sepals.

*Size.*—Considered small.

*Sepal length.*—About 3.5 millimeters.

*Sepal width.*—About 2.5 to about 3.0 millimeters.

*Sepal shape.*—Generally obovate.

*Sepal margin.*—Considered smooth and entire.

*Sepal color.*—Approximately RHS Greyed-Purple Group 182 B.

Anthers:

*Generally.*—Small in size.

*Length.*—About 0.5 millimeters.

*Width.*—About 0.4 millimeters.

*Color.*—Yellow when viewed dorsally and prior to dehiscence, (approximately RHS Yellow-Green Group 150 D).

*Position relative to stigma.*—Generally, the stigma is superior to the anthers by about 1.0 to about 2.0 millimeters.

Pollen production: Pollen is present and has a yellow color, (approximately RHS Yellow-Orange Group 20 A).

Fertility: Self-fertile.

Filaments:

*Size.*—About 8.0 to about 10.0 millimeters in length.

*Color.*—Considered white to a pinkish-white, (RHS White Group N155 D).

Pistil:

*Number.*—Usually one, and only rarely more than one.

*Generally.*—Considered small in size.

*Length.*—About 10.0 to about 12.0 millimeters in length including the ovary.

*Color.*—Considered a very pale green, (approximately RHS Yellow-Green Group 150 D).

*Surface texture.*—The variety has a long pubescent pistil.

*Position relative to petals.*—At flower maturity the stamens grow to be superior to the petals.

*Ovary.*—Generally. — Small in size. Shape. — Drupelet with a narrowing apical margin. Length. — About 3.0 millimeters. Width. — About 2.0 millimeters. Color. — Considered a pale green color, (approximately RHS Yellow-Green Group 145 C). Surface. — Pubescent.

FRUIT

Maturity when described: Ripe condition.

Date of first picking: Approximately Aug. 20, 2019.

Date of last picking: Sep. 2, 2019.

Size: Generally—Considered small.

Average cheek diameter: About 48.0 to about 52.0 millimeters.

Average axial diameter: About 50.0 to about 65.0 millimeters.

Typical weight: About 127.0 grams.

Fruit form: Generally—Considered ovatus. The fruit is generally irregular in symmetry.

Mucron tip: Absent.

Fruit suture: No stitching exists along the suture line.

Suture: Color—Generally, the fruit appears blushed to the same degree as the skin, (approximately RHS Orange-Red Group 34 A).

Ventral surface: Form—Considered even, and uniform in appearance, when it is viewed from the lateral, sutural plane.

Apex: Shape—Acumate.

Base: Shape—The base of the fruit is generally smooth and slightly inaequalis (oblique) with lobing toward the suture plane.

Stem cavity: Generally—It extends in a rounded circular form which is generally considered uniform. The stem cavity is rounded but slightly extended toward the suture. The average depth of the stem cavity is about 5.0 to about 6.0 mm. The average width of the stem cavity is about 10.0 mm. The average length of the stem cavity, when measured in the suturial plane is about 12.0 mm.

Lenticels: None observable on the fruit surface.

Fruit skin:

*Thickness.*—Considered thick, and not tenacious to the flesh at maturity.

*Surface texture.*—Pubescent.

*Taste.*—Non-astringent.

*Tendency to crack.*—Not observed in the previous years of observation and evaluation.

Fruit skin color:

*Blush color.*—Generally speaking, a red blush exists on a majority of the skin of the fruit (approximately RHS Orange-Red Group 34 A) and is more typically present on the portions of the fruit facing the sunlight. The blush of the fruit typically covers approximately 85% to 95% of the fruit skin surface. The percentage of the blush on the fruit skin surface can vary and is generally dependent upon the fruit's exposure to direct sunlight; specific fruit maturity; and the prevailing ecological and cultural conditions under which the fruit was grown.

Ground color: A medium white, (approximately RHS. White Group 155 C). The ground color of the fruit can vary significantly based upon the maturity of the fruit when this measurement is taken and generally gains a lighter and less green cast with higher maturity.

Fruit glossiness: Fruit is considered to be dull. Pubescent.

Fruit stem:

*Size.*—Medium in length, about 6.0 to about 8.0 millimeters.

*Diameter.*—About 2.0 to about 3.0 millimeters.

*Color.*—Pale yellow-green, (approximately RHS Yellow-Green Group N144 C).

Fruit flesh:

*Ripening.*—Considered even.

*Texture.*—Firm, dry and dense. Considered melting in flesh classification.

*Fibers.*—Present and prominent.

*Aroma.*—Slight.

*Eating quality.*—Not commercial.

*Flavor.*—Considered of high acidity.

*Juice production.*—Negligible.

*Brix.*—About 6.0 to about 8.0 degrees.

*Acidity.*—Considered high. Approximately 1.7 titratable acidity at fruit harvest.

*Flesh color.*—It is considered white, (approximately RHS White Group 145 C).

STONE

Type: Considered a freestone.

Size: It is generally considered to be medium small for the species.

Length: Average, about 28.0 to about 31.0 millimeters.

Width: Average, about 20.0 to about 22.0 millimeters.

Diameter: Average, about 14.0 to about 16.0 millimeters.

Form: Roughly ovoid.

Stone base: Shape—The stone is considered shortly attenuate.

Apex: Shape—The stone exhibits a slight acute apex.

Stone surface:

*Surface texture.*—Considered irregularly furrowed toward the apex. Very little pitting is noted.

*Ridges.*—Ridging is generally more prominent and is usually oriented perpendicular relative at the ventral and dorsal margins.

*Ventral edge.*—The ventral edge is generally is described as having adjoining ridges formed from each hemisphere. There a longitudinal groove running alongside this joined ventral suture. These secondary ridges are less prominent and do not always extend from the hilum to the apex.

*Dorsal edge.*—Shape — Generally considered even. The folds of the surface ridges appearing on the external margins often end gently along the suture.

Stone color: The color of a mature, dry stone is generally considered a dull brown, approximately (RHS Greyed-Purple Group 183 B). Stone color can vary considering how recently the fruit has ripened, harvested, degree of oxidation, surface drying and blanching due to exposure sunlight.

Tendency to split: Splitting has rarely been noted.

Kernel:

*Length.*—About 11.0 to about 15.0 millimeters.

*Width.*—About 8.0 to about 11.0 millimeters.

*Thickness.*—About 4.0 to about 5.0 millimeters.

*Size.*—The kernel is considered medium in size.

*Form.*—Considered generally ovoid.

*Kernel surface texture.*—Kernel pellicle is shortly pubescent.

*Color.*—A dark tan (RHS Greyed-Orange Group 165 C).

Use: The present variety 'Warootone' is a rootstock tree providing a degree of vigor reduction for use in orchards established at higher densities than of Nemaguard.

Keeping quality: Not applicable.

Shipping quality: Not applicable.

Resistance to insects and disease: The present variety has exhibited significant resistance to root knot nematodes, resistance to ring nematode and tolerance too lesion nematodes in replicated trials versus control groups of Nemaguard rootstock. The present variety can show some sensitivity to powdery mildew (Podosphaera leucotricha) when the tree is grown above ground in order to provide vegetative cutting material. The present variety also has exhibited resistance to root knot and ring and a degree of tolerance to lesion nematodes in repeated assays. Otherwise the current variety has not intentionally tested to expose or detect any susceptibilities or resistances to any known plant, fruit diseases, insect, frost, winter injury, or other environmental factors.

Although the new variety of rootstock tree possesses the described characteristics when grown under the ecological conditions prevailing near Fowler, Calif., in the Central part of the San Joaquin Valley of California, variations of the usual magnitude, and characteristics incident to changes in growing conditions, fertilization, nutrition, pruning, pest control, frost, climatic variables, and changes in horticultural management are to be expected.

Having thus described and illustrated our new variety of rootstock tree, what we claim is new, and desire to secure by plant Letters Patent is:

1. A new distinct variety of rootstock tree substantially as illustrated and described, and which is characterized principally as to novelty by producing a tree which can be grafted or budded to peach, nectarine, plum, apricot and almond varieties and which reduces the vigor, by approximately 20% when compared to the same varieties of the same age and cultural practices as the rootstock 'Nemaguard' which is the current commercial standard. These observations have been conducted under the conditions prevailing in the San Joaquin Valley of Central California.

* * * * *